United States Patent [19]

Sickler

[11] Patent Number: 5,417,221
[45] Date of Patent: May 23, 1995

[54] METHOD AND APPARATUS FOR DISTINGUISHING ELECTRIC SIGNAL WAVEFORMS

[75] Inventor: Robert L. Sickler, Aloha, Oreg.

[73] Assignee: Psytech, Inc., Portland, Oreg.

[21] Appl. No.: 57,433

[22] Filed: May 7, 1993

Related U.S. Application Data

[63] Continuation of Ser. No. 529,430, May 29, 1990, abandoned.

[51] Int. Cl.⁶ .......................................... A61B 5/0428
[52] U.S. Cl. .................................... 128/696; 128/901
[58] Field of Search .................. 128/696, 703–708, 128/901, 902; 307/517; 328/114, 165

[56] References Cited

U.S. PATENT DOCUMENTS

| | | | |
|---|---|---|---|
| 4,319,581 | 3/1982 | Cutter ................................ | 128/707 |
| 4,325,384 | 4/1982 | Blaster et al. ...................... | 128/708 |
| 4,393,877 | 7/1983 | Imran et al. ....................... | 128/705 |
| 4,617,938 | 10/1986 | Shimoni et al. .................... | 128/708 |
| 4,708,144 | 11/1987 | Hamilton et al. .................. | 128/708 |
| 4,768,144 | 11/1987 | Hamilton et al. .................. | 128/708 |
| 5,038,785 | 8/1991 | Blakeley et al. .................. | 128/696 |

*Primary Examiner*—William E. Kamm
*Attorney, Agent, or Firm*—Olson & Olson

[57] ABSTRACT

The heart rate of a subject during strenuous physical exercise is monitored accurately by feeding the plurality of electric signals of diverse amplitudes generated by transducers engaging the skin of the subject, to a variably controlled gain amplifier to adjust the amplitudes to within a predetermined amplitude range, feeding the adjusted amplitude signals to a slew rate filter formed of a pair of slew rate limiters to compare the slew rates of the adjusted signals, feeding the compared signals to a slew rate limit comparator to separate from the QRS waveforms representing heartbeat of the subject those interfering electric signals having slew rates outside the range of slew rates representing QRS waveforms, and monitoring the QRS waveforms. The separation of interfering signals is achieved with minimum complexity of electronic circuitry and correspondingly reduced cost, by feeding the compared signals also to a microprocessor programmed to recognize as interfering signals those waveforms that have slew rates similar to those of the QRS waveforms but originating as waveforms of substantially greater amplitude and/or of an occurrence rate differing from the uniform recurrence rate of QRS waveforms.

17 Claims, 5 Drawing Sheets

METHOD AND APPARATUS FOR DISTINGUISHING ELECTRIC SIGNAL WAVEFORMS

This application is a continuation of application Ser. No. 07/529,430, filed May 29, 1990, now abandoned.

BACKGROUND OF THE INVENTION

This invention relates to the monitoring of heart rates, and more particularly to a heart rate monitoring method and cardiotachometer capable of monitoring heart rate under difficult or adverse conditions, such as during physical exercise.

Cardiotachometers are used in a wide variety of situations and include a wide variety of types of instruments. The most common uses are in medical related applications for diagnostic and rehabilitation monitoring and in recreational exercise monitoring. Most cardiotachometers available heretofore have performed satisfactorily under the static conditions of diagnostic and rehabilitation monitoring. However, the only ones capable of providing reliable monitoring under the stringent and noisy conditions of physical exercise require the use of chest electrodes. These are uncomfortable and obtrusive and they restrict the range of activity.

A cardiotachometer is made up of three general sections: 1) Transducer; 2) Processing; 3) Readout. A transducer or conductor is attached to a person in a variety of ways and provides an electric output signal. This signal is passed to electronic circuitry which amplifies, filters, detects, counts and provides an electrical output signal representing some measurement of the heart rate. This representation generally is provided as a visual display or auditory signal.

The most common form of transducer, or heartbeat pick-up, is of the chest electrode type. Medical literature has described in great detail the common chest electrode in terms of materials, placement, and other variables. The number of chest electrodes and placement strategy have been defined for some time. The most common variation on the chest electrode is simply to use the electrode as a pick-up on some part of the body other than the chest. Several devices have used electrode pick-ups to sense heart rate related signals through the hands or fingers. These types of electrodes are typically metal buttons of handgrip rings, Common configurations have two electrodes on each hand, or two electrodes on one hand and one electrode in the other hand.

In all cases of the electrode pick-up, electrical signals are detected by making direct contact with skin by the electrode. In many of the chest electrode applications, conductive cream is added between the electrode and the skin to increase conductivity. In exercise applications, chest electrodes are typically held in place by elastic straps that encircle the chest. Alternatively, the electrodes are held in place with tape or adhesive pads surrounding the electrode.

Electrodes are designed to conduct the energy generated by the heart muscle to the inputs of an amplifier. Depending on the placement and configuration of the chest electrodes, the amplitude of the signal varies from 0.1 to 4.0 millivolts. Electrodes used on other parts of the body, such as the hands, result in even smaller and more variable amplitudes. Hand held or finger contact electrodes show much lower amplitude because of the extremity from the heart. In addition, hand held or finger contact show greater variability in conductivity due to contact pressure variations and contact surface contaminants.

Another common method of sensing heart rate uses an infrared light source and detector. This is commonly referred to as a plethysmograph transducer. Blood volume changes associated with heart rate are detected at the extremities by this method. The most common locations for such a transducer are either the fingers or the ear lobe. A clip containing the infrared light source and infrared detector is attached over the extremity. The infrared signal travels through the finger or ear lobe and is sensed by the detector. Variations in blood density in the extremity affect the amount of light passing and thus received by the detector. The detector output is connected to circuitry that amplifies, filters, and compares the signal to an amplitude criteria, counts the "hits" and displays the counts.

A piezoelectric transducer converts mechanical force to electrical energy. This method has been used to detect heart rate at the fingers, and employs a very thin piezoelectric crystal which rests against the finger. Blood volume changes create minute expansions and contractions in the finger, flexing the piezoelectric crystal. The electrical signals generated by movements of the piezoelectric crystal are amplified, filtered, measured against an amplitude criteria, counted and displayed.

Piezoelectric transducers are particularly susceptible to vibration noise. Infrared pick-ups readily respond to mechanical artifacts such as pressure changes. The exercise environment is predominated by both vibratory noise and pressure changes. As a result, these transducer types are at a disadvantage in an exercise application.

Chest electrodes are minimally susceptible to vibratory noise and pressure changes. However, they are generally excluded for use in recreational monitoring because of the logistics involved in their attachment and placement and their obtrusiveness to the user. Electrodes such as wrist straps or hand grips avoid most of the mechanical susceptibility of piezo and infrared pick-ups, but are affected by potential changes generated by voluntary muscle activity and static electricity.

The foregoing illustrates why cardiotachometers available heretofore have not been completely satisfactory in monitoring heartrates during physical exercise because of obtrusiveness or interfering noise.

The general concepts and problems associated with conventional electrocardiography are described in such publications as "Electrocardiology Made Easy" by D. M. Van Wynsberghe and Ronald E. Hammond, in *Carolina Tips*, pages 9–11, volume 47, No. 3, Mar. 1, 1984 of Carolina Biological Supply Company; "R-wave Detection In The Presence Of Muscle Artifacts", by Olivier Y. De Vel, *IEEE Transactions On Biomedical Engineering*, pages 715–717, Volume BME-31, No. 11, November 1984; and "Estimation Of QRS Complex Power Spectra For Design Of A QRS Filter", by Nitish V. Thakor, John G. Webster and Willis J. Tompkins, *IEEE Transactions On Biomedical Engineering*, Pages 702–705, Volume BME-31, No. 11, November 1984.

Typical types of cardiotachometers are disclosed in U.S. Pat. Nos. 4,592,367; 4,616,659; and 4,667,682.

SUMMARY OF THE INVENTION

This invention provides a method and a cardiotachometer which provides accurate monitoring by isolating the R-wave of an ECG complex from extraneous interfering electrical noise primarily by discriminating between the slopes and amplitudes of the R-wave and interfering noise.

It is the principal objective of this invention to provide for the accurate monitoring of heart rates under all conditions of use, including physical exercise.

Another objective of this invention is the provision of the cardiotachometer of the class described that incorporates a microprocessor for minimizing the complication and cost of electronic circuitry for distinguishing noise signals from heartbeat R-waves.

Still another objective of this invention is the provision of the cardiotachometer of the class described that may be adapted for use with a wide variety of exercise devices, including rowing machines, bicycles, treadmills and others.

A further objective of this invention is to provide a cardiotachometer of the class described that is of relatively simplified construction for economical manufacture, compactness, low power consumption for battery operation, and reliability.

The foregoing and other objects and advantages of this invention will appear from the following detailed description, taken in connection with the accompanying drawings of a preferred embodiment.

DESCRIPTION OF THE PREFERRED EMBODIMENT

This invention can be described generally as an electronic signal, time domain pattern recognition system with cardiotachometer information output. Time domain pattern recognition separates desired information from noise by looking for signal time-amplitude characteristics within certain window of predictability. This is contrasted with the more traditional methods of cardiotachometry, which rely on separation of signal from noise by frequency domain filtration. Frequency domain filtration is less successful because the sharp frequency domain filtration, required in exercise cardiotachometry, distorts the time-amplitude (phase) characteristics of the R-wave, thereby losing some of the most predictable, and therefore useful, information.

The electronic circuitry described hereinafter includes an analog front end that provides filtration, primarily time domain filtration, and amplification of the signal. The analog signal is digitized and fed into a microprocessor for software filtration and pattern recognition.

Figure 1:
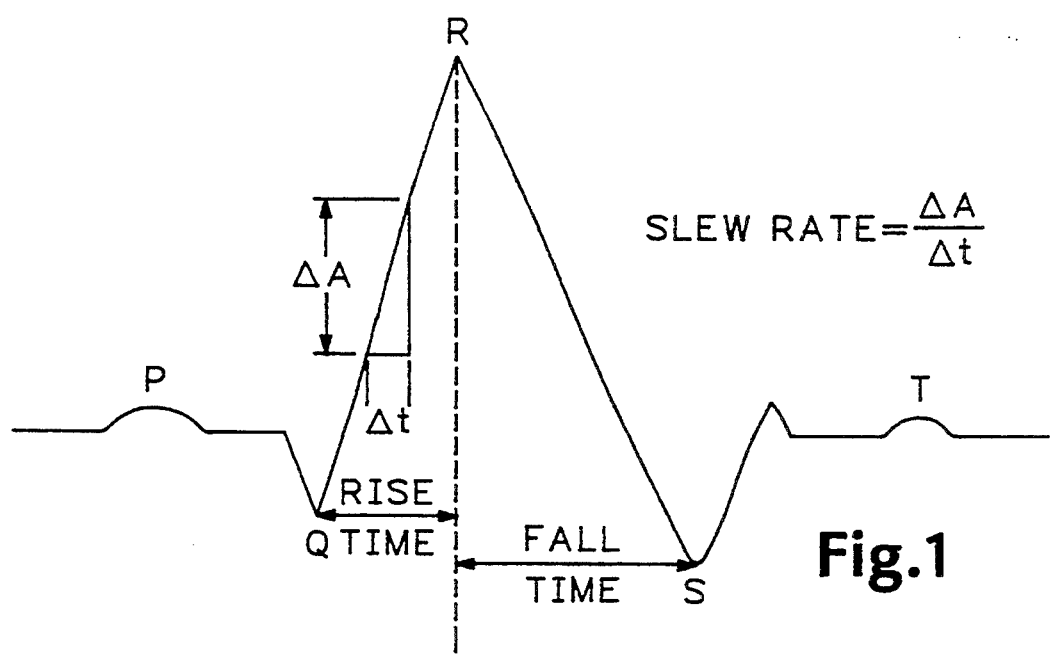
FIG. 1 is an electrocardiogram showing the electrical activity generated by the heart muscle as a PQRST waveform.

Referring now to FIG. 1 of the drawings, the typical medical ECG shows the pattern of electrical activity generated at the heart muscle. This pattern is usually described by the P wave, the QRS complex and the T wave. Because of the unique character and amplitude of the QRS complex, it has been singled out as the primary target of heart rate sensing circuits.

Heretofore, medical grade ECGs maintain as wide a bandwidth as possible in an attempt to preserve the maximum waveform information. The energy spectrum of the QRS complex centers around 11 hertz. The textbook strategy is to provide sufficient amplification of the signal from the electrodes, frequency domain filtering, and level detection. Filtering usually involves a 60 hertz notch filter to remove commercially generated power noise and band-pass filtering around the R-wave frequencies. Detection takes a variety of forms commonly used for signal level detection. Clinical ECGs require wide signal bandwidth in order to maintain high signal fidelity. The disadvantage of these devices is that more noise is passed. Cardiotachometers, in contrast with clinical ECGs, trade signal fidelity for noise rejection by operating with a narrow bandwidth.

Figure 14:
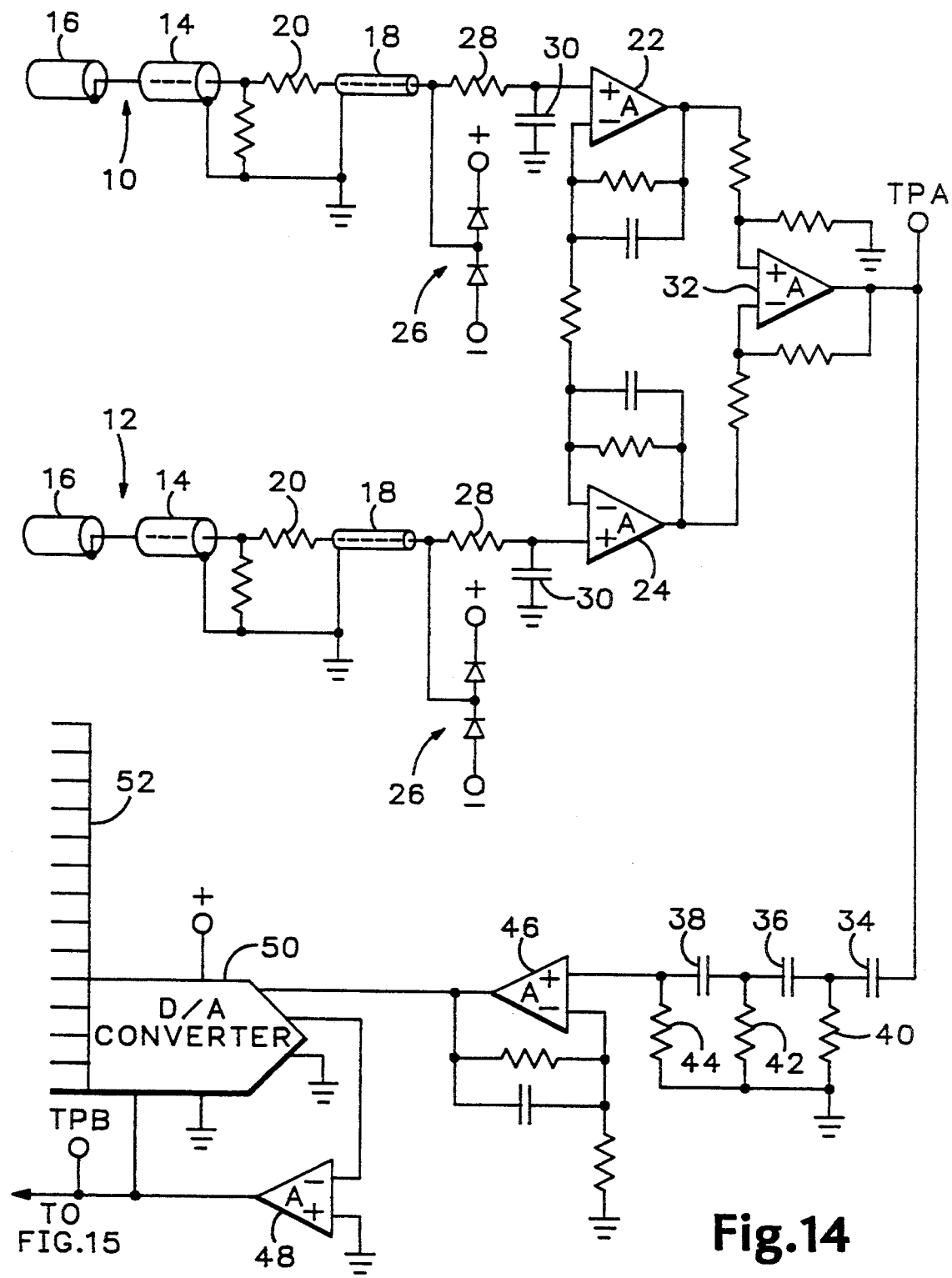
FIG. 14 is a schematic diagram of an electric circuit providing a differential amplifier, a passive high-pass filter and a variable gain stage for the electric circuit of the cardiotachometer of this invention.

Referring now primarily to FIG. 14 of the drawings, there is shown merely for the purpose of illustration, a pair of hand-grip electrodes 10 and 12 that serve to conduct electrical signals generated by the heartbeat. In the embodiment illustrated, the electrodes are in the form of stainless steel tubes configured typically as handgrips for each hand. Each handgrip is split into two tubes 14 and 16 on the same axis. One tube 14 on each hand serves as a ground reference, while the other tube 16 serves as the signal pickup. Shielded cable 18 attached to each handgrip pair, conducts the signal from the electrodes to the circuitry. A resistance 20 at the tubes is designed to provide low pass passive filtering in conjunction with the cable capacitance. The 3 db point of this filter is at 10 KHz.

The shielded cables run directly to the input section 21 (FIG. 13) which includes differential preamplifiers 22 and 24. These amplifiers amplify the signal to a level sufficient for further filtration and provide common mode rejection for immunity to environmental electrical noise, predominantly 60 Hz. Diode assemblies 26 at the inputs of the preamplifiers protect against large static potential differences at the electrodes. A 1 KHz low pass, passive filter, provided by resistor 28 and capacitor 30, precede each preamplifier input. High input impedence is provided to reduce susceptibility to large impedance variations at the skin/electrode connection. The gain through the amplifiers is 100x.

The difference of each electrode signal is preamplified and summed by another CMOS operational amplifier 32. The output of this summing amplifier 32 is fed directly to a 3-pole passive high pass filter 33 (FIG. 13) formed of capacitors 34, 36 and 38 and resistors 40, 42 and 44. The 3 db point of this unity gain filter is at 2 Hz. This filter is designed to minimize time distortion of the R-wave by implemention in a low group delay and with its corner frequency sufficiently removed from the lowest frequency components of the R-wave. The filter functions to reduce the P, S and T components of the ECG waveform (FIG. 1) as well as low frequency noise from the signal.

Figure 13:
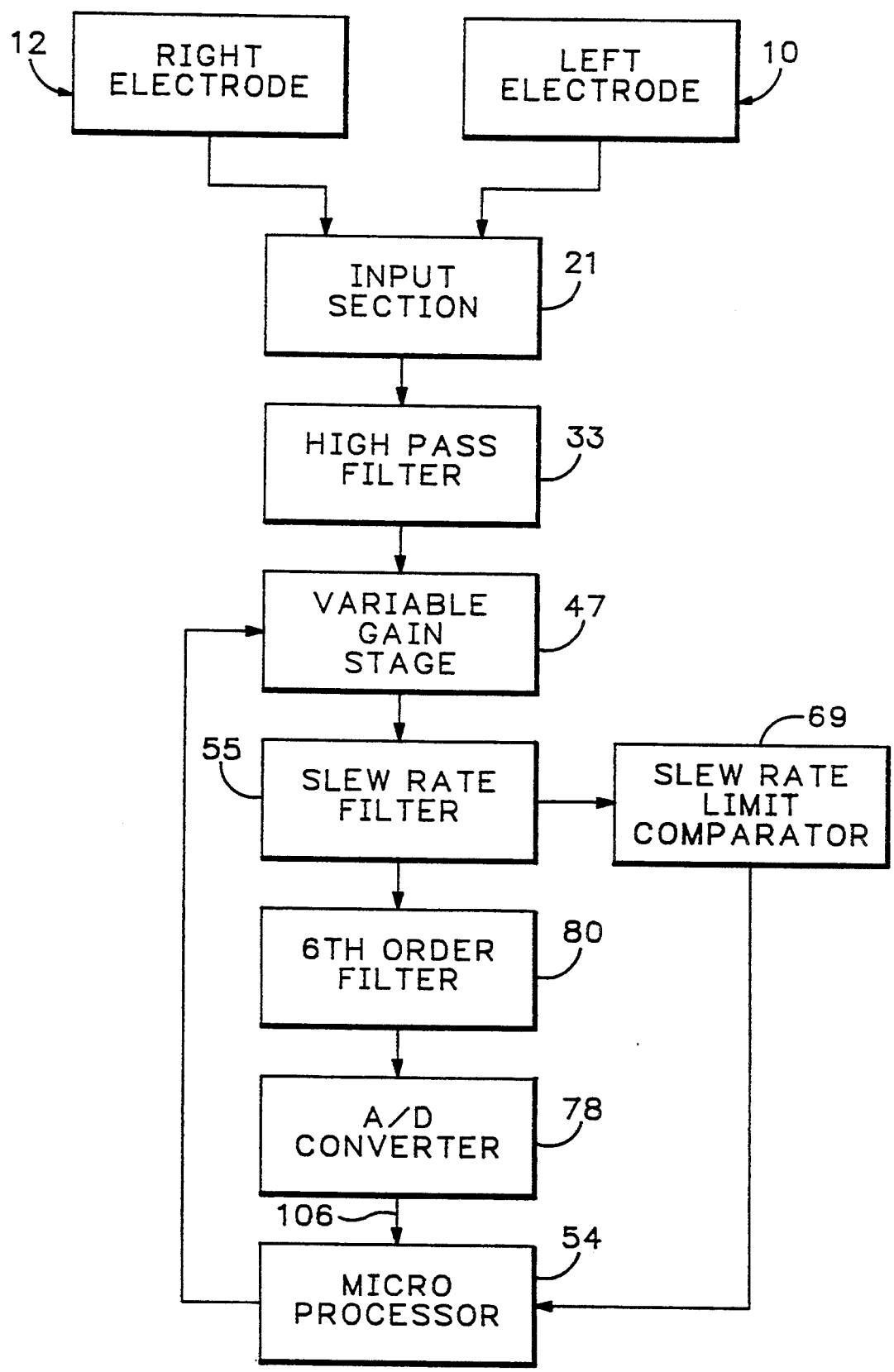
FIG. 13 is a block diagram of an electric circuit for the cardiotachometer of this invention.

The output of the high pass filter is fed directly into a buffer CMOS amplifier 46 with 10x gain. From the buffer amplifier the signal is fed directly into a variably controlled gain stage 47 (FIG. 13) which includes amplifier 48 (FIG. 14). The gain is controlled digitally by an eight bit digital-to-analog converter 50. The digital word controlling the converter comes directly from the data bus 52 of the system microprocessor 54 (FIG. 13). The converter provides 252 steps of gain control from 256/258 (minimum amplification) to 256/5 (maximum amplification).

Figure 3:
FIG. 3 is the same portion of an electrocardiogram of FIG. 2 showing typical noise generated during exercise.
Figure 8:
FIG. 8 is a portion of an electrocardiogram showing a filtered ECG plus noise waveform, on a compressed time scale, before amplitude normalization.
Figure 9:
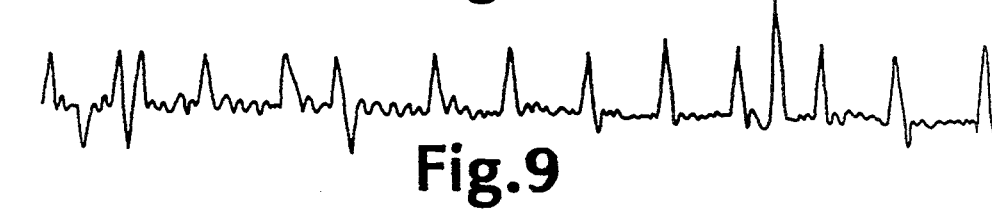
FIG. 9 is the portion of the electrocardiogram of FIG. 8 showing the normalization of the waveform amplitudes by operation of the variable gain stage of FIG. 14.
Figure 10:
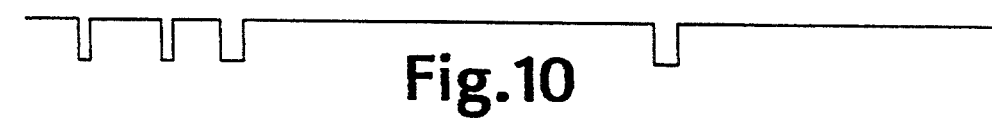
FIG. 10 shows the waveform of the output of the slew rate comparator of FIG. 15, as it is responding to its input waveform of FIG. 7.

The variable gain stage functions to normalize the R-wave amplitude by increasing the gain to increase the amplitude of those R-waves that are below a predetermined minimum and by decreasing the gain to reduce the amplitude of those R-waves that exceed a predetermined maximum. This is illustrated in FIGS. 8 and 9, wherein the change in amplitude between minimum and maximum R-waves after normalization is about one third the amplitude range of a typical exercising person (FIG. 3). This variable gain section is critical to the functioning of the next following slew rate section, the most novel aspect of the circuitry.

The preceding variable amplification stage works in conjunction with the slew rate section, as does the subsequent pattern recognition function of the microprocessor 54. Classically, the R-wave is chosen for cardiotachometer detection schemes primarily because its amplitude is greater than that of other components of the ECG waveform. However, in an exercise environment, noise is routinely encountered which has very similar frequency and amplitude characteristics, making conventional frequency domain filtration unworkable.

Of all the parameters of the QRS complex, the time duration of the rise and fall of the R-wave shows the least variability. Reliance on pattern recognition makes these parameters a natural choice for detection emphasis. The success of a pattern recognition approach is directly related to the predictability of the signal. Predictability makes signal detection more likely in a noisy environment. For these reasons the focus of this invention is on the time domain characteristics of the R-wave, and this emphasis has dictated the use of the slew rate filter.

A signal slew rate is defined as a signal's change in amplitude divided by the change in time, as illustrated in FIG. 1. R-wave peak amplitude normally varies over time. The variable gain stage functions to maintain a constant peak amplitude over time of the R-wave. Fixing the R-wave peak amplitude makes the slew rate of the R-wave constant. Accordingly, since the signal slew rates are very predictable, the slew rate filter can be designed to begin rejecting noise which is of a slew rate of about two times that of the R-wave slew rate. If the R-wave amplitude were not constant, the rejection slew rates would be more in the range 8 to 10 times the R-wave slew rate. Operating with the cut-off of the slew rate closer to the slew rate of the R-wave greatly improves the signal to noise ratio. As a result, the filter can better detect signals in an environment dominated by electrical noise generated by voluntary muscle contractions, motion artifact and static electricity. These types of noise are readily generated during exercise.

Figure 11A:
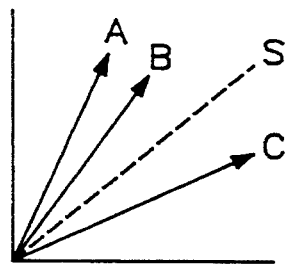
FIGS. 11a and 11b are graphic representations illustrating the function of a slew rate limiter incorporated in the electronic circuitry of FIG. 15.

The slew rate filter of this invention functions as a slew rate filter in contrast to a slew rate limiter. For example, the output C in FIG. 11b of a slew rate limiter is equal to its input C in FIG. 11a with signals below the limiter's limiting slew rates. Input signals, such as A and B in FIG. 11a, with slew rates above the circuit's limiting slew rate S produce outputs A and B in FIG. 11b equal to but not greater than the circuit's limit.

Figure 12A:
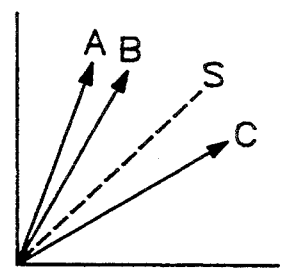
FIGS. 12a and 12b are graphic representations illustrating the function of a slew rate filter incorporated in the electronic circuitry of FIG. 15.
Figure 12B:
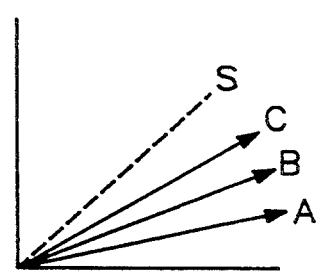
Figure 16:
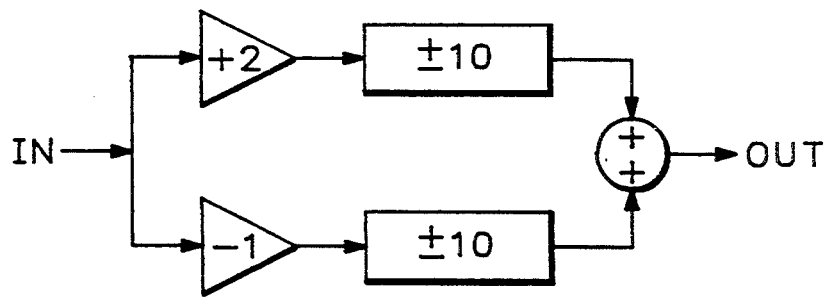
FIG. 16 is a block diagram of the slew rate filter component.
Figure 2:
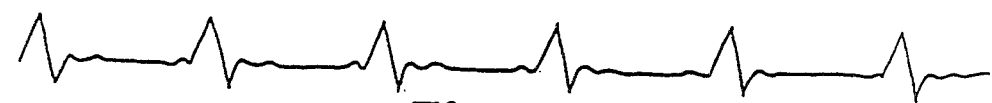
FIG. 2 is a portion of an electrocardiogram showing a succession of ECG complexes.

A slew rate filter behaves similarly up to its cut-off point, but input signals such as A and B in FIG. 12a with slew rates above the cut-offs, rather than being limited to the limit value S, are actually attenuated to slew rates A and B in FIG. 12b.

Figure 15:
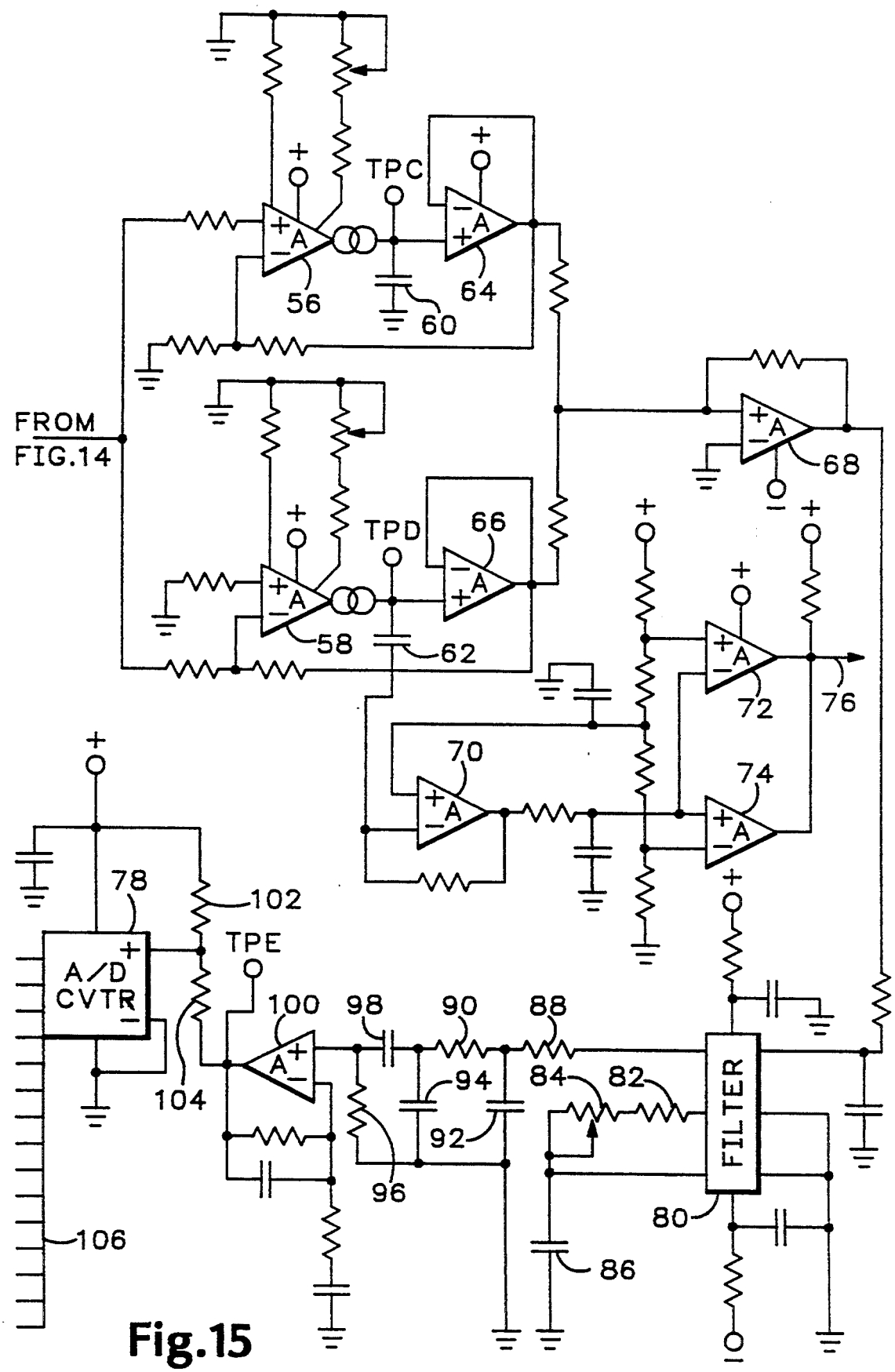
FIG. 15 is schematic diagram of an electric circuit providing a slew rate filter component and an analog-digital converter component of the electric circuit of the cardiotachometer of this invention.

The slew rate filter 55 (FIG. 13) of the present invention is formed by combining the outputs of two slew rate limiters with a summing amplifier. Slew rate limiting is accomplished by charging and discharging a capacitance (in microfarads) with a limited charge and discharge current (in microamperes). Voltage slew rate is current divided by capacitance. This is implemented by feeding the signal from amplifier 48 (FIG. 14) to the inputs of amplifiers 58 and 58 (FIG. 15) which have limited output currents, and using the outputs of the amplifiers to charge and discharge the capacitors 80 and For signals with slew rates equal to or below the value I (the amplifier's limiting current), divided by C, the circuit's output voltage follows the input voltage. For signals with slew rates above I divided by C, the circuit's output voltage slew rate is equal to I divided by C. This accomplishes slew rate limiting.

Referring to FIG. 18 of the drawings, in the slew rate filter of this invention, the input signal is fed to two parallel slew rate limiters. One limiter is preceded with a gain of +2 and the other limiter is preceded with a gain of −1. For input signals with slew rates below the limiting slew rate (C of FIG. 11a), as noted above, the output simply follows the input (FIG. 11b). Accordingly, the circuit then functions as two parallel amplifiers 64 and 66 (FIG. 15) with the same input signal. When the output of these amplifiers are summed at summing amplifier 68, the output is +2 −1, equalling In order to describe the operation of the slew rate filter, its operation is broken into three distinct regions. The first is the cut-off region, where input signals are at slew rates above the filter cut-off, and hence the filter has virtually no output. The second is the attenuation region, where the slew rate of the output is less than that at the input. The third is the unity gain region, where the signal passes through unchanged.

For purposes of explanation, numerical values will be assigned to the input signal's slew rate. In this example, signals with slew rates less than 2 are in the filter's unity gain region. Signals with slew rates between 2 and 10 are in the filter's attenuation region. Signals with slew rates at or above 10 are in the filter's cut-off region.

Above the cut-off region, assume an input signal with a slew rate of ±10. This is amplified by a gain of +2 in one amplifier and a gain of −1 in the other amplifier. The amplifier with a gain of +2 drives a limiter with a limit of ±10, and hence the limiter's output is +10. The amplifier with a gain of −1 drives a slew rate limiter with a limit of ±10, and hence its output is −10. (The limiters are configured in a bipolar fashion, so that the outputs can be of positive or negative polarity.) When these two outputs are summed, the total output is defined by the equation: $+10+(-10)=0$. Accordingly, it can be seen that signals with slew rates exceeding the slew rate filter's cut-off value will result in no output.

In the attenuating region, and assuming a signal with a slew rate of 7, the signal will, in one channel, be amplified by +2, giving it a value of 14. This is fed to a limiter with a limit of ±10, whereby the resulting output is a slew rate of +10. The signal, when fed to the other channel, has a gain of −1, and since its limit is ±10, gives a result of −7. When these signals are summed, the result is a signal slew rate of 3. Since the resulting slew rate is less than the input slew rate, this constitutes attenuation.

In the unity gain region, and assuming a signal with a slew rate of 2, this signal is amplified in one channel which has a gain of 2, giving a value of 4. This is output from the slew rate limiter with a value of 4, since it is less than 10. The output of the channel with a gain of −1, is −2. This is output from its limiter with a value of −2. When these two outputs are summed, the output is $+4-2=2$.

A slew rate filter has the advantage of reducing noise more effectively than a slew rate limiter. The major disadvantage of a filter is that in the attenuation range of the filter, noise slew rates greater than the signal's slew rate can be attenuated to values close to the signal slew rate. In the present invention, a circuit is provided which can detect those occurrences and provide a signal to aid in the subsequent pattern recognition. This is accomplished with a slew rate limit comparator 69 (FIG. 13) which detects the action of the slew rate filter without affecting its performance. The slew rate limiting capacitor 62, rather than being connected to ground as capacitor 60 is, is held at virtual ac ground by feedback from an operational amplifier 70. The output voltage of this amplifier is proportional to the current through the capacitor 62. The output is connected to the inputs of comparator amplifiers 72 and 74 which are set to switch when the slew rate limiting current is achieved.

Knowing that the slew rate limit has been reached can allow discrimination between noise and signal in those cases where they would have similar characteristics at the filter's output. The output of the comparators 72 and 74 is fed through conductor 76 to the microprocessor 54 for this purpose.

The output of the analog section of the circuit is fed to an A/D converter 78. As in all A/D converters, this output must be filtered to meet the Nyquist sampling criteria. That is, the highest frequency of input signal to the converter must not exceed one half the sampling frequency of the conversion, and the amplitude of highest frequency should not exceed the least significant bit (one step). Such a filter is referred to as an anti-aliasing filter.

Cost and power drain constraints, typical of this type of instrument, necessitate a low A/D sampling rate. Since the slew rate filter is inherently a first order filter in the frequency domain, it does not have sufficient steepness for the signal to meet the Nyquist criteria. An additional higher order frequency filter is provided for anti-aliasing. This frequency domain filter is dedicated for anti-aliasing and not required for separating R-wave components from noise. As a result, its group delay effects do not interfere with pattern recognition detection. This frequency domain filter is implemented with a single integrated circuit switched capacitor filter 80. It has a sixth order Butterworth characteristic and a corner frequency of 30 Hz which is determined by the resistors 82 and 84 and capacitor 86.

Following this filter 80, is a passive, two pole, low pass filter, with a corner frequency of 50 Hz, provided by resistors 88 and 90 and capacitors 92 and 94. This low pass filter removes clock artifact normally present at the output of the switched capacitor filter 80. Following the low pass filter is a single passive high pass filter provided by resistor 96 and capacitor 98, to block DC. Following this high pass filter is an amplifier 100 with a gain of 10 and a two resistor level shifter 102 and 104 to meet the input requirements of the A/D converter.

The eight TTL signals from the A/D converter 78 are connected to the data bus 106 of the system microprocessor 54. This is an industry standard eight-bit, stand-alone microprocessor. The microprocessor is also connected to the variable gain stage 47.

Figure 4:
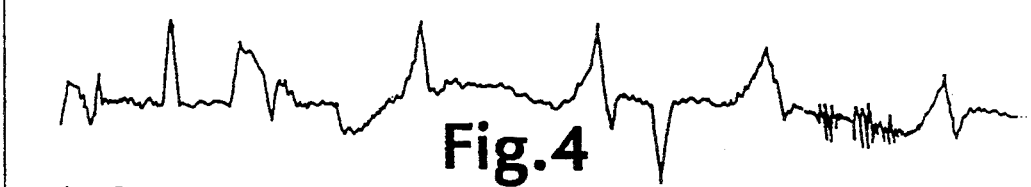
FIG. 4 is a portion of an electrocardiogram showing the summation of the waveforms of FIGS. 2 and 3.
Figure 5:
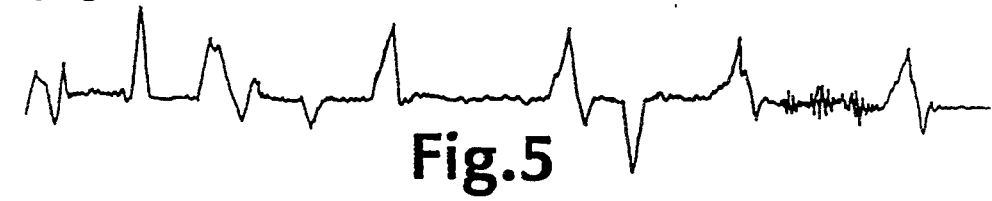
FIG. 5 is the portion of the electrocardiogram of FIG. 4 showing the low frequency noise component removed by operation of the high pass filter of FIG. 14.

In the operation of the system described hereinbefore, let it be assumed that the heart rate of a person is to be monitored while exercising on a treadmill or other exercise device which incorporates the hand-held electrodes 10 and 12. Thus, as the exercise proceeds, an electrocardiogram waveform pattern, in the configuration illustrated in FIG. 3, is produced as a summation of noise and normal ECG. These signals are delivered to the differential preamplifiers 22 and 24 where high and low frequency noise components are reduced somewhat, and the signals are amplified to a level sufficient to afford further filtration and to provide common mode rejection for immunity to environmental electrical noise, predominantly 60 Hz. The amplified signals then are passed from amplifier 32 to the high pass filter 34–44 that functions to reduce baseline shift of the waveform and also to substantially eliminate the low frequency noise signal. This is illustrated in FIG. 4.

The filtered signals then are passed to the variable gain stage 48 which functions to normalize the R-wave amplitude from the levels illustrated in FIG. 8 to the levels illustrated in FIG. 9. Thus, the R-waves and noise peaks are adjusted to lie within a relatively narrow range. One of them is shown to be still quite high, because the variable gain stage has not had time to respond. Peaks such as this will be eliminated by the slew rate filter.

Figure 6:
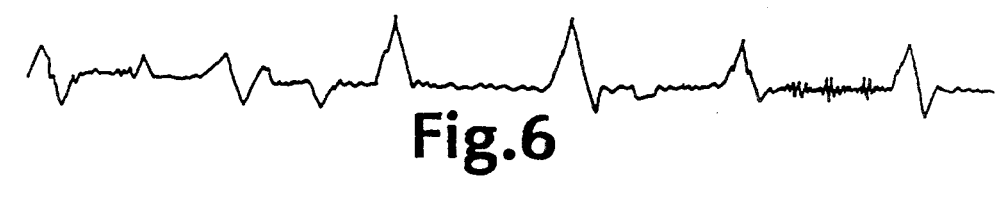
FIG. 6 is the portion of the electrocardiogram of FIG. 5 showing the reduction in amplitude of the high amplitude waveform of FIG. 5 by operation of the slew rate filter of FIG. 15.

The normalized signals then are passed to the slew rate filter that functions to reject those noise signals having slew rates at least twice that of the R-wave slew rate. FIG. 6 shows the output of the slew rate filter.

Noise with slew rates in a particular narrow range, greater than the slew rate, may be attenuated to values close to the R-wave's slew rate. For example, let it be assumed that a noise signal is present having an amplitude much higher than the normalized R-wave. The slew rate filter attenuates the noise signal progressively to the same level as the R-wave, whereby it looks like the R-wave.

Figure 11B:
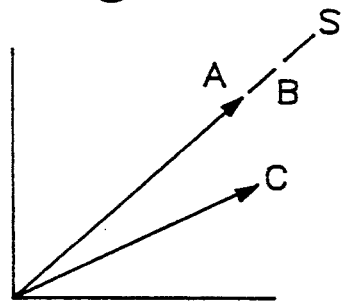

The slew limit detector is used to prevent such signals from confusing the subsequent pattern recognition. The slew limit detector senses the operation of the slew rate filter by measuring the current through capacitor 62. This is done with amplifier 70 which holds the bottom of capacitor 62 at a.c. ground and converts the current to voltage (FIG. 11b). The output voltage of the operational amplifier 70 is connected to the comparator inputs which are set to switch when the slew rate limiting current is achieved. The output of these comparators is fed to the microprocessor 54 for discriminating between noise and R-wave signals which have similar characteristics.

The attenuation region of the slew rate filter can be narrowed to reduce the chances of noise being attenuated to R-wave slew rates to a point where such an occurrence would be statistically insignificant. The penalty would be the requirement of costly, high precision filters. In this application it was deemed more cost effective to detect such signals via the slew rate detectors.

Figure 7:
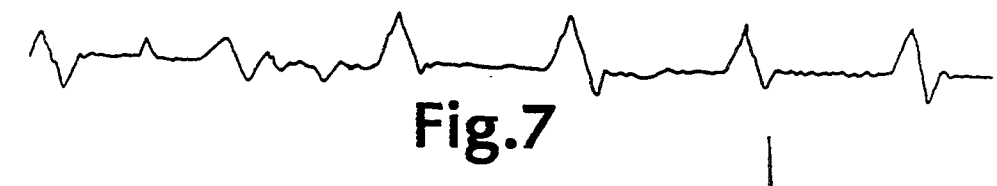
FIG. 7 is the portion of the electrocardiogram of FIG. 6 showing the broad band noise component reduced by operation of the low pass filter of FIG. 15.

FIG. 7 illustrates the output of the high frequency switched capacitor filter 80. It shows high frequency jitters removed, leaving essentially just R-wave signals to be presented to the A/D converter 78. The microprocessor 54 thus sees the digitized version of FIG. 7.

The output of the A/D converter appears as an 8-bit word on the processor bus 106. The word changes following the input signal at the converter sampling rate. This, together with the output of the slew limit detector, is the information that is processed to give the cardiotachometer result.

It is by this means that noise signals generated during exercising, are prevented from interfering with the recognition of true R-waves and the accurate monitoring of heart rate during strenuous exercising.

It will be apparent that since the cardiotachometer described hereinbefore is capable of accurately monitoring heart rate during strenuous physical exercise, it is also capable of monitoring heart rate under the less strenuous conditions of diagnostic and rehabilitation monitoring.

Although the foregoing illustration is directed to heart rate monitoring, the method and apparatus of this invention also may be used for impulse noise reduction in other applications, such as reduction of static in audio communications. Slew rate filtering also may be employed where sensitive environmental sensors are used in noisy environments, such as manufacturing process control and security systems. Many other applications will be apparent to those skilled in the art.

It will also be apparent to those skilled in the art that various changes may be made in the method steps and structural details described hereinbefore without departing from the spirit of this invention and the scope of the appended claims.

I claim:

1. Apparatus for identifying a desired electric signal waveform from extraneous electric interference signal waveforms, comprising
   a) means for obtaining a plurality of electrical waveforms of diverse amplitude some of which represent desired electric signal waveforms and others of which represent interference waveforms of noise and other extraneous sources which interfere with recognition of the desired electric signal waveforms,
   b) means for adjusting the amplitudes of said waveforms to within a predetermined range of amplitudes,
   c) means for separating from desired adjusted electric signal waveforms those interference waveforms having slew rates above and below a predetermined range of slew rates representing desired electric signal waveforms, and
   d) means for indicating the presence of desired electric signal waveforms.

2. The apparatus of claim 1 wherein the separating means comprises a slew rate filter formed of a pair of slew rate limiters and an algebraic summing amplifier, the limiters having a common input for receiving said electric signal waveforms of adjusted amplitude, and each output being connected to said algebraic summing amplifier.

3. The apparatus of claim 2 wherein the means for separating desired waveforms from interference waveforms comprises a slew rate limit comparator having an output connected to means for indicating the presence of desired electric signal waveforms, and an input connected to the output of one of the slew rate limiters.

4. Apparatus for identifying a desired electric signal waveform from extraneous electric interference signal waveforms, comprising
   a) means for obtaining a plurality of electrical waveforms of diverse amplitude some of which represent desired electric signal waveforms and others of which represent interference waveforms of noise and other extraneous sources which interfere with recognition of the desired electric signal waveforms,
   b) means for adjusting the amplitudes of said waveforms to within a predetermined range of amplitudes, said means including a variably controlled gain amplifier having an input for receiving said plurality of waveforms of diverse amplitudes, digital gain control means connected to the amplifier for controlling the gain of the amplifier, and a microprocessor connected to the digital gain control means and having a program for adjusting the amplitudes of the desired electrical signal to within said predetermined range, the amplifier having an output connected to separating means,
   c) separating means for separating from desired adjusted electric signal waveforms those interference waveforms having slew rates above and below a predetermined range of slew rates representing desired electric signal waveforms, said separating means comprising a slew rate filter formed of a pair of slew rate limiters and an algebraic summing amplifier, the limiters having a common input for receiving said electrical waveforms of adjusted amplitude and each output connected to said algebraic summing amplifier,
   d) slew rate limit comparator means having an output connected to the input of said microprocessor, and an input connected to the output of one of the slew rate limiters, and
   e) means for identifying the slew rates of said desired separated waveforms, said means comprising said microprocessor and an analog-to-digital converter connected thereto, the microprocessor having an output connected to the digital gain control means, an input connected to the output of the slew rate comparator means, and an output for indicating the presence of desired electric signal waveforms, the microprocessor having a program, first for separating the desired electric signal waveforms by identifying as interference waveforms certain of the waveforms differing from the desired electric signal waveforms in at least one of the characteristics of time duration of the rise and fall of the waveforms, the amplitude of the waveforms, and the recurrence rate of the waveforms, second for controlling the digital gain control means, third for detecting the output of the slew rate comparator means, and fourth for enabling the output of the microprocessor to indicate the presence of the desired electric signal waveforms.

5. Apparatus for identifying the desired QRS electric signal waveform of the heartbeat of a subject from extraneous electric interference signal waveforms, comprising
   a) means for obtaining a plurality of electrical waveforms of diverse amplitude some of which represent desired QRS electric signal waveforms and others of which represent interference waveforms of noise and other extraneous sources which interfere with recognition of the desired QRS electric signal waveforms,
   b) means for adjusting the amplitude of said waveforms to within a predetermined range of amplitudes,
   c) means for separating from desired adjusted QRS electric signal waveforms those interfering waveforms having slew rates above and below a predetermined range of slew rates representing desired QRS electric signal waveforms, said separating means comprising a slew rate limit comparator having an output connected to means for indicating the presence of desired electric signal waveforms, and an input connected to the output of one of the slew rate limiters, and
   d) means for indicating the presence of the desired separated QRS waveforms.

6. Apparatus for identifying the desired QRS electric signal waveform of the heartbeat of a subject from extraneous electric interference signal waveforms, comprising
   a) means for obtaining a plurality of electrical waveforms of diverse amplitude some of which represent desired QRS electric signal waveforms and others of which represent interference waveforms of noise and other extraneous sources which interfere with recognition of the desired QRS electric signal waveforms,
   b) means for adjusting the amplitude of said waveforms to within a predetermined range of amplitudes, said adjusting means including a variable controlled gain amplifier having an input for receiving said plurality of waveforms of diverse amplitudes, digital gain control means connected to the amplifier for controlling the gain of the amplifier, and a microprocessor connected to the digital gain control means and having a program for adjusting the amplitudes of the QRS waveform to within a predetermined range, the amplifier having an output connected to separating means,
   c) means for separating from desired adjusted QRS electric signal waveforms those interference waveforms having slew rates above and below a predetermined range of slew rates representing desired QRS electric signal waveforms, said separating means comprising a slew rate filter formed of a pair of slew rate limiters and an algebraic summing amplifier, the limiters having a common input for receiving said electrical waveforms of adjusted amplitude and each output connected to said algebraic summing amplifier,
   d) slew rate limit comparator means having an output connected to the input of the microprocessor, and an input connected to the output of one of the slew rate limiters,
   e) said microprocessor connected to an analog-to-digital converter and having an output connected to the digital gain control means, an input connected to the output of the slew rate comparator means, and an output for indicating the presence of desired electric signal waveforms, the microprocessor having a program, first for separating the QRS waveforms by identifying as interference waveforms certain of the waveforms differing from the QRS waveforms in at least one of the characteristics of time duration of the rise and fall of the waveforms, the amplitude of the waveforms, and the recurrence rate of the waveforms, second for controlling the digital-to-analog converter, third for detecting the output of the slew rate comparator means, and fourth for providing output indicating the presence of desired separated QRS waveforms.

7. The method of identifying a desired electric signal waveform from extraneous electric interference signal waveforms, comprising:
   a) obtaining a plurality of electrical waveforms of diverse amplitudes some of which represent the desired electric signal waveforms and others of which represent interference waveforms of noise and other extraneous sources which interfere with identification of the desired electric signal waveforms,
   b) adjusting the amplitudes of said waveforms to within a predetermined range of amplitudes,
   c) comparing the slew rates of said adjusted waveforms,
   d) separating from desired electric signal waveforms those interference waveforms having slew rates above and below a predetermined range of slew rates representing desired electric signal waveforms, and
   e) providing output indicating the presence of desired separated electric signal waveforms.

8. The method of claim 7 wherein the separating of interference waveforms is achieved by identifying as interference waveforms certain of the waveforms differing from the desired electric signal waveforms in at least one of the characteristics of the time duration of the rise and fall of the waveforms and the amplitude of the waveforms.

9. The method of claim 7 wherein the separating of interference waveforms is achieved by feeding the electrical waveforms to a microprocessor programmed to indentify as interference waveforms certain of the waveforms differing from the desired electrical signal waveforms in at least one of the characteristics of the time duration of the rise and fall of the waveforms, the amplitude of the waveforms, and the recurrence rate of the waveforms.

10. The method of claim 7 for identifying the desired QRS electric signal waveform of the heartbeat of a subject from extraneous electric interference signal waveforms, wherein the obtaining of the electrical waveforms from a subject is achieved by contacting the skin of an exercising subject with transducer means capable of producing electrical signals representing said QRS and interference waveforms.

11. The method of claim 7 for identifying the desired QRS electric signal waveform of the heartbeat of a subject from extraneous electric interference signal waveforms, wherein the separating of interference waveforms is achieved by identifying as interference waveforms certain of the waveforms differing from the QRS waveforms in at least one of the characteristics of the time duration of the rise and fall of the waveforms, the amplitude of the waveforms and the recurrence rate of the waveforms.

12. The method of claim 7 for identifying the desired QRS electric signal waveform of the heartbeat of a subject from extraneous electric interference signal waveforms, wherein the separating of interference waveforms is achieved by feeding the electrical waveforms to a microprocessor having a program for indentifying as interference waveforms certain of the waveforms differing from the QRS waveforms in at least one of the characteristics of the time duration of the rise and fall of the waveforms, the amplitude of the waveforms, and the recurrence rate of the waveforms.

13. The method of claim 7 for identifying the desired QRS electric signal waveform of the heartbeat of a subject from extraneous electric interference signal waveforms, wherein
  a) the obtaining of electrical waveforms from the subject is achieved by contacting the skin of an exercising subject with transducer means capable of producing electrical signals representing the QRS waveform and interference waveforms representing muscle artifact, and
  b) the separating of interfering waveforms is achieved by feeding the electrical waveforms to a microprocessor having a program for identifying as waveforms certain of the waveforms differing from the QRS waveforms in at least one of the characteristics of the time duration of the rise and fall of the waveforms, the amplitude of the waveforms, and the recurrence rate of the waveforms.

14. Apparatus for identifying a desired electric signal waveform from extraneous electric interference signal waveforms, comprising
  a) means for obtaining a plurality of electrical waveforms of diverse amplitude some of which represent desired electric signal waveforms and others of which represent interference waveforms of noise and other extraneous sources which interfere with identification of the desired electric signal waveforms,
  b) means for adjusting the amplitude of said waveforms to within a predetermined range of amplitudes,
  c) means for separating from desired adjusted electric signal waveforms those interference waveforms having slew rates above and below a predetermined range of slew rates representing desired electric signal waveforms, and
  d) means for indicating the presence of desired electric signal waveforms having slew rates within said predetermined range of slew rates.

15. The apparatus of claim 14 wherein the means for adjusting the amplitudes of said waveforms includes a variably
  controlled gain amplifier having an input for receiving said plurality of waveforms of diverse amplitudes, digital gain control means connected to the amplifier for controlling the gain of the amplifier, and a microprocessor connected to the digital gain control means and having a program for adjusting the amplitudes of the desired electrical signal to within said predetermined range, the amplifier having an output connected to the separating means.

16. The apparatus of claim 14 for indicating the presence of the desired electric signal waveforms wherein the desired electric signal is the QRS waveform of the heartbeat of a subject, and wherein the means for obtaining electrical waveforms from a subject comprises transducer means for contacting the skin of a subject during physical exercise and capable of conducting electrical signals representing said waveforms.

17. The apparatus of claim 14 wherein the transducer means comprise hand-grip electrodes.

* * * * *

UNITED STATES PATENT AND TRADEMARK OFFICE
CERTIFICATE OF CORRECTION

PATENT NO. : 5,417,221
DATED : 23 May 1995
INVENTOR(S) : ROBERT L. SICKLER

It is certified that error appears in the above-identified patent and that said Letters Patent is hereby corrected as shown below:

Col. 1, line 47, "rings," should read --rings.--

" 4, line 15, "within certain" should read --within a certain--.

" 5, line 36, "256/258" should read --256/256--.

" 6, line 43, "58 and 58" should read --56 and 58--.

" 6, line 45, "80 and" should read --60 and 62--.

" 6, line 52, "18" should read --16--.

" 6, line 62, "equalling" should read --equalling 1.--

" 12, line 65, "indentify" should read --identify--.

Signed and Sealed this

Eighteenth Day of July, 1995

Attest:

BRUCE LEHMAN

*Attesting Officer*  *Commissioner of Patents and Trademarks*